United States Patent [19]

Wickens et al.

[11] Patent Number: 5,750,667

[45] Date of Patent: May 12, 1998

[54] SYSTEM TO DETECT PROTEIN-RNA INTERACTIONS

[75] Inventors: Marvin P. Wickens, Madison, Wis.; Stanley Fields, Setauket, N.Y.

[73] Assignee: Wisconsin Alumni Research Foundation, Madison, Wis.

[21] Appl. No.: 747,183

[22] Filed: Nov. 12, 1996

Related U.S. Application Data

[62] Division of Ser. No. 409,561, Mar. 23, 1995, Pat. No. 5,610,015.

[51] Int. Cl.⁶ .............................. C07H 21/02; C12Q 1/68
[52] U.S. Cl. .............................................. 536/23.1; 435/6
[58] Field of Search ................................ 536/23.1; 435/6

[56] References Cited

U.S. PATENT DOCUMENTS 5,283,173  2/1994  Fields et al. ................................ 435/6

OTHER PUBLICATIONS

Chien, C.-T., et al., "The two-hybrid system: A method to identify and clone genes for proteins that interact with a protein of interest." *Proc. Natl. Acad. Sci. USA* 88:9578–9582, 1991.

Fields, S., et al., "A novel genetic system to detect protein-protein interactions." *Nature* 340:245–246, 1989.

Frankel, A.D., et al., "RNA–Protein Interactions," *Cell* 67:1041–1046, 1991.

"Introducing the Matchmaker Two–Hybrid System," Clontech Advertisement, date unkown.

Spencer et al. Conrolling signal transduction with synthetic ligands Science vol. 262 1019–1024, 1993.

Silar et al. New shuttle vectors for direct cloning in *Saccharomyces cerevisiae* Gene vol. 104 99–102, 1991.

Stripecke et al. Proteins binding to 5' untranslated region sites: a general mechanism for translational regulation of mRNAs in human and yeast cells Mol. Cell. Biol. vol. 14 5898–5909, 1994.

Mattaj RNA recognition: A family matter? Cell vol. 73 837–840, 1993.

Fields et al. The two–hybrid system: an assay for protein–protein interactions Trends in Genetics vol. 10 286–292, 1994.

Good et al. Yeast expression vectors using RNA polymerase III promoters Gene vol. 151 209–214, 1994.

*Primary Examiner*—James Ketter
*Assistant Examiner*—John S. Brusca
*Attorney, Agent, or Firm*—Quarles & Brady

[57] ABSTRACT

A method for detecting an interaction between an RNA-binding protein and a test RNA molecule is disclosed. This method comprises providing a host cell containing a detectable gene. The detectable gene expresses a detectable protein when the detectable gene is activated by an amino acid sequence including a transcriptional activation domain when the transcriptional activation domain is in sufficient proximity to the detectable gene. First, second and third chimeric genes are also provided. The first chimeric gene comprises a DNA-binding domain that recognizes a binding site on the detectable gene in the host cell and a first RNA-binding domain. The second chimeric gene comprises a transcriptional activation domain and a second RNA-binding domain. The third chimeric gene comprises a first RNA sequence capable of binding to either the first or second RNA-binding and a second RNA sequence to be tested for interaction with the RNA-binding protein not bound to the first RNA sequence. Interaction between both the first RNA-binding domain and the hybrid RNA and the second RNA-binding domain and the hybrid RNA in the host cell causes expression of the detectable gene.

1 Claim, 2 Drawing Sheets

```
GUUUUACGUU UGAGGCCUCG UGGCGCACAU GGUACGCUGU GGUGCUCGCG GCUGGGAACG

AAACUCUGGG AGCUGCGAUU GGCAGAAUUC CUGCAGCCCG GGUCUCUCUG GUUAGACCAG
                                             ---------------------
AUCUGAGCCU GGGAGCUCUC UGGCUAACUA GGAACCCGAU AGCUUGCAUG CCUGCAGGUC
----------------------------------------
GACUCUAGAA AACAUGAGGA UCACCCAUGU CUGCAGGUCG ACUCUAGAAA ACAUGAGGAU
           =========================================================
CACCCAUGUC UGCAGGUCGA CUCUAGAGGA UCAUCGAAUU CCCCCAUAUC CAACUUCCAA
=========
UUUAAUCUUU CUUUUU
```

--- TAR SEQUENCE

=== TWO TANDEM R17 COAT PROTEIN BINDING SITES

FIG. 2

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:1:

CAGGTGGATC CATATGGCTT CTAACTTTAC T        3 1

( 2 ) INFORMATION FOR SEQ ID NO:2:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:2:

TGCTAGGATC CTTAGTAGAT GCCGGAGTT        2 9

( 2 ) INFORMATION FOR SEQ ID NO:3:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:3:

AGTCGGGATC CTAATGGAGC CAGTAGATCC T        3 1

( 2 ) INFORMATION FOR SEQ ID NO:4:

( i ) SEQUENCE CHARACTERISTICS:

```
                ( A ) LENGTH: 32 base pairs
                ( B ) TYPE: nucleic acid
                ( C ) STRANDEDNESS: single
                ( D ) TOPOLOGY: linear ( i i ) MOLECULE TYPE: oligonucleotide ( x i ) SEQUENCE DESCRIPTION: SEQ ID NO:4:

GTGACGGATC CTTACTGCTT TGATAGAGAA AC                                                32

( 2 ) INFORMATION FOR SEQ ID NO:5:

( i ) SEQUENCE CHARACTERISTICS:
                ( A ) LENGTH: 42 base pairs
                ( B ) TYPE: nucleic acid
                ( C ) STRANDEDNESS: single
                ( D ) TOPOLOGY: linear ( i i ) MOLECULE TYPE: oligonucleotide ( x i ) SEQUENCE DESCRIPTION: SEQ ID NO:5:

CCCGGGTCTC TCTGGTTAGA CCAGATCTGA GCCTGGGAGC TC                                     42

( 2 ) INFORMATION FOR SEQ ID NO:6:

( i ) SEQUENCE CHARACTERISTICS:
                ( A ) LENGTH: 43 base pairs
                ( B ) TYPE: nucleic acid
                ( C ) STRANDEDNESS: single
                ( D ) TOPOLOGY: linear ( i i ) MOLECULE TYPE: oligonucleotide ( x i ) SEQUENCE DESCRIPTION: SEQ ID NO:6:

ATCGGGTTCC CTAGTTAGCC AGAGAGCTCC CAGGCTCAGA TCT                                    43

( 2 ) INFORMATION FOR SEQ ID NO:7:

( i ) SEQUENCE CHARACTERISTICS:
                ( A ) LENGTH: 316 base pairs
                ( B ) TYPE: nucleic acid
                ( C ) STRANDEDNESS: single
                ( D ) TOPOLOGY: linear ( i i ) MOLECULE TYPE: other nucleic acid ( x i ) SEQUENCE DESCRIPTION: SEQ ID NO:7:

GUUUUACGUU UGAGGCCUCG UGGCGCACAU GGUACGCUGU GGUGCUCGCG GCUGGGAACG                   60

AAACUCUGGG AGCUGCGAUU GGCAGAAUUC CUGCAGCCCG GGUCUCUCUG GUUAGACCAG                  120

AUCUGAGCCU GGGAGCUCUC UGGCUAACUA GGAACCCGAU AGCUUGCAUG CCUGCAGGUC                  180

GACUCUAGAA AACAUGAGGA UCACCCAUGU CUGCAGGUCG ACUCUAGAAA ACAUGAGGAU                  240

CACCCAUGUC UGCAGGUCGA CUCUAGAGGA UCAUCGAAUU CCCCAUAUC CAACUUCCAA                   300

UUUAAUCUUU CUUUUU                                                                  316
```

SYSTEM TO DETECT PROTEIN-RNA INTERACTIONS

This is a division of application Ser. No. 08/409,561 filed Mar. 23, 1995 U.S. Pat. No. 5,610,015.

FIELD OF THE INVENTION

The present invention in general relates to a system to detect protein-RNA interactions. In particular, the present invention relates to a method for detecting protein-RNA interactions by use of an in vivo system using chimeric genes encoding hybrid proteins and a hybrid RNA.

BACKGROUND

Protein-RNA Interaction

Interactions between proteins and RNA molecules are of biological and clinical importance. Proteins are complex macromolecules made up of covalently linked chains of amino acids. Each protein assumes a unique three dimensional shape determined principally by its sequence of amino acids. Many proteins consist of smaller units termed domains, which are continuous stretches of amino acids able to fold independently from the rest of the protein. Some of the important forms of proteins are as enzymes, polypeptide hormones, nutrient transporters, structural components of the cell, hemoglobins, antibodies, nucleoproteins, and components of viruses.

RNA (ribonucleic acid) is the transcription product of a DNA sequence. RNA is typically classified as either ribosomal RNA (rRNA), transfer RNA (tRNA), or messenger RNA (mRNA). RNAs are generally synthesized by enzymes that copy the nucleotide sequences from a DNA template, and the vast majority participate in protein synthesis. Ribosomal RNA is found in ribosomes which are the particles on which protein synthesis takes place. Messenger RNA is an intermediary sequence that transfers genetic information from the DNA to the ribosome. Transfer RNA carries amino acids to the site of protein synthesis. Other RNAs may be present in the prokaryotic or eukaryotic cell but occur in smaller amounts and may participate in functions such as DNA synthesis and the cutting and splicing of RNA sequences.

A certain subgroup of proteins is known to bind RNA molecules. For example, Frankel, et al. (*Cell* 67:1041–1046, 1991) reviewed RNA-protein interactions. Protein-RNA interactions are important in a variety of biological and clinical contexts. These interactions include infections by RNA viruses, translation and mRNA splicing. Therefore, understanding these interactions and selecting inhibitors and activators is essential when seeking RNAs as pharmaceuticals and planning rational drug design.

A variety of approaches have been used to study RNA-protein interactions. In vitro approaches include physical methods, such as x-ray crystallography, and biochemical assays, such as chemical and enzymatic footprinting, gel retardation and filter binding experiments (summarized in Frankel et al., supra). In vivo approaches to assaying RNA-protein interactions in a generally applicable manner, relying merely on binding and not on any other biological property of the molecule, are few. Binding of an RNA-binding protein to an appropriately placed site, at a suitable position upstream of the translation initiation codon in a reporter gene, can cause detectable repression of a reporter gene in yeast in vivo (Stripecke, et al., *Molec. and Cell. Biol.* 14:5898–5909, 1994).

Transcriptional Activation through Separated Domains

There is evidence that transcription can be activated through the use of two functional domains of a transcription factor: a domain that recognizes and binds to a specific site on the DNA and a domain that is necessary for activation, as reported by Keegan, et al., *Science* 231:699–407 (1986) and Ma and Ptashne, *Cell* 48:847–853 (1987). The transcriptional activation domain is thought to function by contacting other proteins involved in transcription. The DNA-binding domain appears to function to position the transcriptional activation domain on the target gene which is to be transcribed. In several cases now known, these two functions (DNA-binding and activation) reside on separate proteins. One protein binds to the DNA, and the other protein, which activates transcription, binds to the DNA-bound protein, as reported by Tijan and Maniatis, *Cell* 77:5–8, 1994.

Transcriptional activation has been studied using the GAL4 protein of the yeast *Saccharomyces cerevisiae*. The GAL4 protein is a transcriptional activator required for the expression of genes encoding enzymes of galactose utilization, see Johnston, *Microbiol. Rev.* 51:458–476 (1987). It consists of an N-terminal domain which binds to specific DNA sequences designated $UAS_G$ ("UAS" stands for upstream activation site; "G" indicates the galactose genes) and a C-terminal domain containing acidic regions, which is necessary to activate transcription, see Keegan, et al. (1986), supra, and Ma and Ptashne (1987), supra. As discussed by Keegan, et al., the N-terminal domain binds to DNA in a sequence-specific manner but fails to activate transcription. The C-terminal domain cannot activate transcription because it fails to localize the $UAS_G$, see for example, Brent and Ptashne, *Cell* 43:729–736 (1985). However, Ma and Ptashne have reported (*Cell* 51:113–119, 1987; *Cell* 55:443–446, 1988) that when both the GAL4 N-terminal domain and C-terminal domain are fused together in the same protein, transcriptional activity is induced.

Other proteins also function as transcriptional activators via the same mechanism. For example, the GCN4 protein of *Saccharomyces cerevisiae* (as reported by Hope and Struhl, *Cell* 46:885–894, 1986), the LEX A protein (as a LEXA-GAL4 protein reported by Brent and Ptashne, *Cell* 43:729–736, 1985), the VP16 protein of herpes simplex virus (as a GAL4-VP16 hybrid reported by Sadowski, et al., *Nature* 335:563–564, 1988), the ADR1 protein of *Saccharomyces cerevisiae* as reported by Thukral, et al., *Molecular and Cellular Biology* 9:2360–2369, 1989 and the human estrogen receptor, as discussed by Kumar, et al., *Cell* 51:941–951, 1987 contain separable domains for DNA binding and for maximal transcriptional activation.

U.S. Pat. No. 5,283,173 (Fields and Song, issued Feb. 1, 1994) discloses a system to detect protein—protein interactions through use of chimeric genes which express hybrid proteins. This system uses the separation of transcription factors described above in an assay system.

None of the aforementioned articles suggest such a genetic system designed to detect protein-RNA interactions in vivo using transcriptional activation as an assay.

SUMMARY OF THE INVENTION

In one embodiment, the present invention is a method of detecting protein-RNA interactions. The method begins with a host cell that contains a detectable gene expressing a detectable protein. The detectable gene is activated by an amino acid sequence including a transcriptional activation domain when the transcriptional activation domain is in sufficient proximity to the detectable gene.

The host cell also contains three different chimeric genes. The first chimeric gene is capable of being expressed in the host cell and encodes a first hybrid protein. The first hybrid protein comprises a DNA-binding domain that recognizes a binding site on the detectable gene in the host cell and a first RNA-binding domain. (When we refer to an RNA-binding "domain", we mean an amino acid sequence that is capable of binding an RNA molecule. This domain may be a fragment of a larger protein or may comprise an entire protein.)

The second chimeric gene is also capable of being expressed in the host cell and comprises a DNA sequence that encodes a second hybrid protein. The second hybrid protein comprises a transcriptional activation domain and a second RNA-binding domain.

The third chimeric gene is capable of being transcribed to generate a hybrid RNA in the host cell. The hybrid RNA comprises a first RNA sequence capable of binding to either the first or second RNA-binding domain and a second RNA sequence to be tested for interaction with the RNA-binding domain that is not bound to the first RNA sequence. Interaction between both the first RNA-binding domain and the hybrid RNA and the second RNA-binding domain and the hybrid RNA causes the transcriptional activation domain to activate transcription of the detectable gene.

After subjecting the host cell to conditions under which the first hybrid protein, the second hybrid protein, and the hybrid RNA are expressed in sufficient quantity for the detectable gene to be activated, one determines whether the detectable gene has been expressed to a degree greater than expression in the absence of an interaction between both the first RNA-binding protein and the hybrid RNA and the second RNA-binding protein and the hybrid RNA. If the detectable gene has been expressed to a greater degree, this indicates that an RNA-protein interaction has taken place.

It is an advantage of this invention that either one of the RNA-binding proteins or either the first or second sequence of the hybrid RNA may be tested. One might have a specific RNA-binding protein and determine which of many different RNA sequences bound to the protein, or one might have a particular RNA sequence and determine which of many RNA-binding proteins bound to that specific RNA sequence.

It is an advantage of this method that a multiplicity of proteins can be simultaneously tested to determine whether any interact with a known RNA molecule. Similarly, a multiplicity of RNAs can be simultaneously tested to determine whether any interact with a known RNA-binding protein.

For example, a DNA fragment encoding the DNA-binding domain may be fused to a DNA fragment encoding a known RNA-binding protein in order to provide the first chimeric gene. For the second chimeric gene, a library of plasmids can be constructed which may include, for example, a total cDNA library fused to the DNA sequence encoding the activation domain. The third chimeric gene may encode a hybrid RNA comprising a first RNA sequence that is known to bind the RNA-binding protein encoded by the first chimeric gene and a second RNA sequence that binds an uncharacterized protein.

The CDNA library is introduced into cells carrying the first and third chimeric genes. If any individual plasmid from the library encodes a protein that is capable of interacting with the second RNA sequence, a positive signal will be obtained. Similarly, a library of plasmids that are constructed to include a first RNA sequence that is known to bind the RNA-binding domain encoded by either the first or second chimeric gene and a sequence selected from a cDNA library could be used for the third chimeric gene if one wished to examine a variety of RNA sequences.

This method has the additional advantage that when and interaction between the RNA and protein occurs, the gene for the newly identified protein or RNA is readily available from the cDNA library. Therefore, the system can be of value in the identification of new genes. For example, one can identify genes that interact with known biologically active RNA molecules.

Accordingly, it is an object of the present invention to provide a genetic system and related testing kit for detecting RNA-protein interactions.

Another embodiment of the present invention is a method for testing conditions for modulation of RNA-protein interactions. One performs the method described above in the presence of the substance to be tested as a modulator of RNA-protein interaction. One would compare the results of this method with control conditions.

Yet another embodiment of the present invention is a method for detecting an interaction between an RNA molecule and a test RNA molecule. In this method, two different hybrid RNAs are prepared. The third chimeric gene encodes a first hybrid RNA that contains a first RNA sequence capable of binding to the first RNA-binding domain and a second RNA sequence. A fourth chimeric gene is provided that encodes a second hybrid RNA that contains a third RNA sequence capable of binding to the second RNA-binding domain and a fourth RNA sequence to be tested for interaction with the second RNA sequence. Interaction between the first RNA-binding domain and the first hybrid RNA, the second RNA-binding domain and the second hybrid RNA, and the third RNA sequence and the fourth RNA sequence in the host cell causes the transcriptional activation domain to activate transcription of the detectable gene.

Another embodiment of the present invention is a method for comparing the protein-binding affinity of the first test RNA sequence and a second test RNA sequence. One would perform the method described above with variants of the second RNA sequence. One could then compare expression levels of the detectable gene to determine which test RNA sequence bound the RNA-binding protein with highest affinity. By these comparisons, one could optimize an RNA sequence for high affinity binding.

It is an object of the present invention is to provide an assay that is useful to test a multiplicity of proteins or RNAs.

It is another object of the present invention to provide a method for detection of protein-RNA interactions in which the nucleic acid fragments that encode the interacting proteins or interacting RNAs are immediately available when a positive test occurs.

Another object of the present invention is to provide a method for the identification of new genes.

Another object of the present invention is to provide a method that can be used in the detection, isolation, and design of peptides and RNAs to be used therapeutically. In particular, the present invention allows a comparison of the protein-binding affinity of test RNA sequences.

It is another object of the present invention to provide a system for testing affinity reagents for protein or RNA purification.

Other objects, advantages and features of the present invention will become apparent after studying the accompanying figures, specification and claims.

DESCRIPTION OF THE FIGURES

FIG. 1A diagrams native GAL4 activation of a reporter gene. FIG. 1B diagrams the relationship between the first hybrid protein, the hybrid RNA and the second hybrid protein. FIG. 1C diagrams the interaction between hybrid proteins and hybrid RNA in reconstituting GAL4 activity.

FIG. 2 is a diagram of the predicted RNA sequence of a hybrid RNA transcribed from pIIIExRPR vectors SEQ ID NO.:7.

DESCRIPTION OF THE INVENTION

1. In General

RNA-protein interactions are pivotal in fundamental cellular processes, such as translation, RNA splicing, regulation of key decisions in early development, and infection by RNA viruses. However, in spite of the central importance of these interactions, few in vivo approaches are available to analyze them. We provide herein a genetic method to detect and analyze RNA-protein interactions.

The following components are required. One must first provide a host cell containing a detectable gene. By "detectable" we mean that one of skill in the art could assay for an expression product (RNA or protein). This detectable gene is activated by an amino sequence that includes a transcriptional activation domain when the transcriptional activation domain is in sufficient proximity to the detectable gene. An example of such a detectable gene and activation by transcriptional activation domain is shown in FIG. 1.

Second, fusion of a DNA-binding domain (such as the above-described N-terminal domain of the GAL4 protein) to a well-characterized RNA-binding domain creates a hybrid protein that can be targeted to the promoter of a reporter gene. We refer to this chimeric gene as the "first chimeric gene."

Third, fusion of a transcriptional activation domain (such as the above-described C-terminal domain of the GAL4 protein) to a second RNA-binding domain (which is to be analyzed) creates a second hybrid protein that can activate expression of the reporter when localized to the promoter. We refer to this second fusion as the "second chimeric gene."

Fourth, in order to position the activation domain hybrid at the reporter gene, a hybrid RNA is generated that contains recognition sites for the two RNA-binding domains. We refer to this third gene construct as the "third chimeric gene."

Figure 1A:
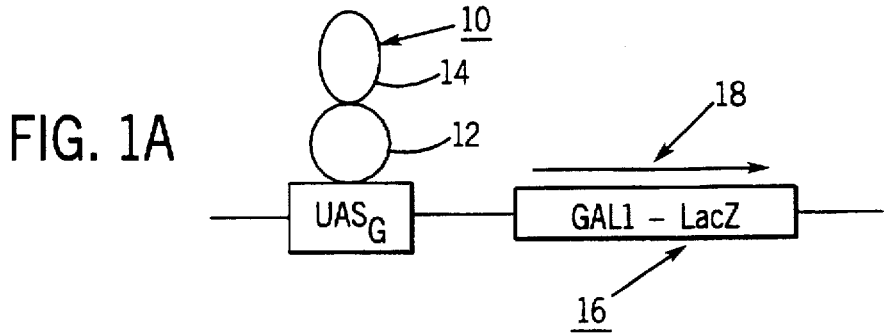
FIG. 1A–C schematically represent transcriptional activation by reconstitution of GAL4 activity.

The basic strategy of this testing method is shown in FIG. 1. FIG. 1A schematically illustrates the binding of the native GAL4 protein 10 having a DNA-binding domain 12 and a transcriptional activation domain 14. The native GAL4 protein 10, containing both domains 14 and 12, is a potent activator of transcription of the GAL1-lacZ gene 16 when yeast are grown on galactose-containing media. Transcription of the GAL1-lacZ gene 16 is indicated by the arrow 18. The lacZ gene encodes β-galactosidase, which may easily be detected and measured by calorimetric analysis. Of course, other marker genes known to those of skill in the art may replace the lacZ sequence.

Figure 1B:
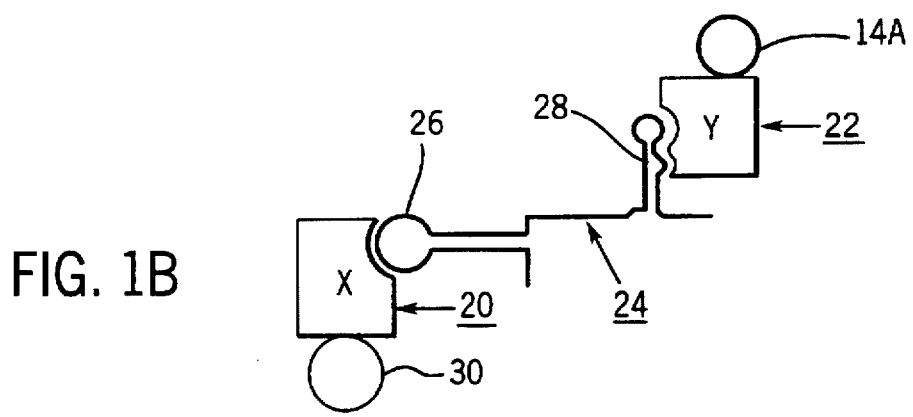

FIG. 1B schematically illustrates the present invention by illustrating the interaction between the two hybrid proteins, 20 and 22 and the hybrid RNA 24. The first hybrid protein 20 contains a first RNA-binding domain X and a DNA-binding domain 30. The GAL4 DNA binding domain 12 illustrated in FIG. 1A could have been used in FIG. 1B and in the examples below. A preferable DNA-binding domain 30 is the LEX A protein, and a preferable DNA sequence for LEX A binding is the Lex A op (Giniger, et al., *Cell* 40:767–774, 1985). One of skill in the art would know of many other DNA-binding domains and DNA sequences that could substitute for the LEX A/LexA op combination and the GAL4 DNA-binding protein/UAS$_G$ combination.

The second hybrid protein 22 contains a second RNA-binding domain Y and the GAL4 activation domain 14A. The hybrid RNA 24 contains a first RNA sequence 26 which binds to the first RNA-binding protein X and a second RNA sequence 28 which binds to the second RNA-binding protein Y.

Figure 1C:
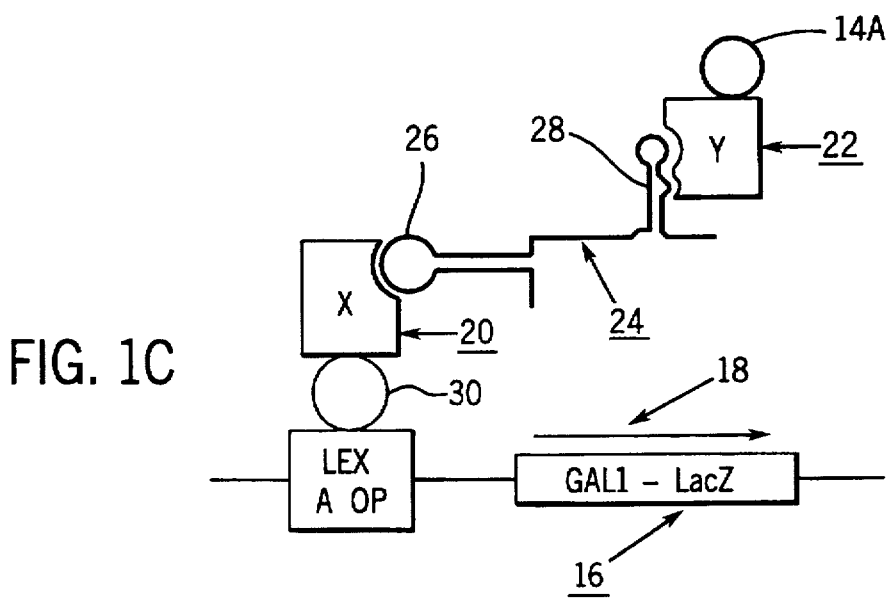

Neither of these hybrid proteins 20 or 22 or hybrid RNA 24, alone, is able to activate transcription. The interaction of proteins X and Y with hybrid RNA 24, as illustrated in FIG. 1C, allows the portion of the GAL4 activation domain 14A to be brought into sufficient proximity to the DNA-binding domain 30, allowing transcription 18 of GAL1-lacZ gene 16 to occur. Transcriptional activation can be determined by measuring β-galactosidase activity.

This system may be used to identify, isolate and characterize either a specific RNA that binds to a known RNA-binding protein or a specific RNA-binding protein that binds a specific RNA. In the first case, one would have a defined hybrid RNA and test the first or second RNA-binding protein. In the second case, one would have a defined first or second RNA-binding protein and test the hybrid RNA.

The system is dependent on a number of conditions to properly carry out the method of this invention. The first interacting protein X must not, itself, carry an activation domain for the marker. Otherwise the activation domain would allow transcription of the marker gene as soon as the vector encoding only the GAL4 DNA-binding domain fused to the first interacting protein X is introduced. The interaction between the first test protein X and the second test protein Y must be capable of occurring within the yeast nucleus. The GAL4 activation domain portion of the hybrid containing the second test protein Y must be accessible to the transcription machinery of the cell to allow transcription of the marker gene. Protein X should not bind to protein Y. The hybrid RNA should not itself act as a potent transcriptional activation domain.

Should any of these conditions not exist, the system may be modified for use by such procedures as constructing hybrids that carry only portions of the interacting proteins X and Y and thus meet these conditions.

Using the HIV TAT protein/TAR sequence interaction as an example, we demonstrate below in the Examples that the complex of a hybrid RNA with the two hybrid proteins results in transcriptional activation. This system should have numerous applications in the identification of RNA-binding proteins and RNAS.

First, this method should be useful for identifying and cloning the genes for RNA-binding proteins that recognize biologically important RNA sequences. For example, short RNA sequences have been identified that control the processing, translation, location, and stability of specific mRNAs, and the packaging and infectivity of RNA viruses. The proteins that interact with such sequences may be identified using the large variety of existing libraries of genomic and cDNA sequences in activation domain vectors.

Such libraries are already in use for the detection of protein—protein interactions in the two-hybrid assay.

Although our example used only the lacZ gene as reporter, other reporter genes that allow direct selection can be used to facilitate library screening. Additionally, the gene encoding the DNA-binding domain/coat protein hybrid can be integrated into the reporter strain, thereby requiring the transformation of only two plasmids.

Second, it should be possible to generate a library of hybrid RNAs, each carrying the coat protein-binding sites fused to some short cellular RNA. Such a library may enable the identification, for example, of specific mRNAs that bind to a defined protein.

Third, the system should be capable of defining domains, as well as single amino acid residues or nucleotides, that are necessary in vivo for either a newly detected or previously characterized interaction.

Fourth, this technology may allow an in vivo method to identify or to assay synthetic RNA oligonucleotides with selective affinity for defined proteins, analogous to in vitro approaches that exploit reiterative selections. (Tuerk, et al., *Science* 249:505–510, 1990; Ellington, et al., *Nature* 346:818–822.)

Fifth, it may be possible to extend this method in order to generate a four-hybrid system for the analysis of RNA—RNA interactions. In this approach, the two protein hybrids would be fixed, e.g. a DNA-binding domain hybrid fused with MS2 coat protein and an activation domain hybrid with TAT. Two hybrid RNAs would be generated, one containing MS2 coat protein binding sites fused to an RNA sequence, X', and the other containing the TAR element fused to another RNA sequence, Y'. Interaction between the X' and Y' RNAs may result in transcriptional activation.

Sixth, this assay provides a facile means to screen in viva for modulators of a known RNA-protein interaction. For example, using the plasmids described here, modulators of the interaction between TAT and the TAR element should result in decreased or increased transcriptional activity.

The present invention could therefore be used to identify both inhibitors (antagonists) or stimulators (agonists) of a specific RNA-protein interaction. The molecules that might be tested, in either case, include any molecules that can be introduced into the cell without killing it. The cell would already have a functional arrangement of all three chimeric genes, in which all the components were fixed, and the expression of a reporter gene would require the two RNA-protein interactions. Inhibitors would prevent expression of the reporter gene; agonists would enhance it. The molecules to be tested could be of any sort. The molecules to be tested would fall into two broad classes, based on how they would be introduced to the cell.

(1) Direct application to the cell or addition to the growth medium.

Substances that would be tested in this way include organic and inorganic molecules of any type. Perhaps some of the more profitable sorts of molecules to examine would be a wide variety of naturally occurring organic molecules (such as certain antibiotics or small organic molecules extracted from plants, fungi, etc.), synthetic organic molecules, or crude extracts of microorganisms. In all of these cases, cells would be exposed to a range of concentrations of the substance, or substances, and the level of expression of the reporter gene monitored.

(2) Introduction to the cell via cloned DNA.

Proteins and peptides would best be introduced to the cell via a DNA encoding them. Thus, the cell would be transformed with a library of DNAs, each one of which encodes a different peptide or protein. The peptides or proteins could be artificial, generated from random sequence, or could be derived from naturally occurring proteins (as in a cDNA library). Using cloned DNA libraries, one could screen a very large number of sequences. However, any specific peptide might work in the sort of assay described in (1).

One advantageous approach to take for the screening of inhibitors would be the use of a "counter selection" strategy. By counter selection we mean that one would be able to specifically identify cells that do not express the reporter. For example, the interaction of the three chimeric genes could turn on GAL1-URA3, which is toxic to yeast growing on 5-FOA. The presence of an inhibitor that would disrupt this RNA-protein interaction would be detected by survival of the cell. This approach is particularly advantageous if one couples the inhibitor screen with a combinatorial library where one can identify the specific compound of interest.

Transcriptional activation in the three-hybrid system relies only on the physical, and not the biological, properties of the RNA. The RNA-protein interactions are assayed in an entirely foreign context, having nothing to do with the normal function of the RNA molecule. As a result, a wide variety of RNA-protein interactions should be amenable to analysis.

2. Suitable Host Cells

The method of the present invention first provides a host cell, preferably a yeast cell and most preferably *Saccharomyces cerevisiae* or *Schizosaccharomyces pombe*. The host cell will contain a detectable gene having a binding site for the DNA-binding domain of the transcriptional activator, such that the detectable gene expresses a detectable protein when the detectable gene is transcriptionally activated. Such activation occurs when the transcriptional activation domain of the transcriptional activator is brought into sufficient proximity of the DNA-binding domain of the transcriptional activator.

Since other eukaryotic cells use a mechanism similar to that of yeast for transcription, other eukaryotic cells such as HeLa cells can be used instead of yeast to test for RNA-protein interactions. The reporter gene function can be served by any of a large variety of genes, such as genes encoding drug resistance or metabolic enzymes. The functions of GAL4 can be served by any protein domains capable of transcriptional activation.

3. Design of the Three Chimeric Genes

A first chimeric gene is provided which is capable of being expressed in the host cell. The first chimeric gene may be present in a chromosome of the host cell. The first chimeric gene comprises a DNA sequence that encodes a first hybrid protein. The first hybrid protein contains a DNA-binding domain that recognizes the binding site on the detectable gene in the host cell. The first hybrid protein also contains a first RNA-binding domain. This domain may be tested for interaction with a test RNA or may be known to bind a specific RNA.

A second chimeric gene is provided which is also capable of being expressed in the host cell. The second chimeric gene contains a DNA sequence that encodes a second hybrid protein. The second hybrid protein contains a transcriptional activation domain. The second hybrid protein also contains a second RNA-binding protein or a protein fragment. The second RNA-binding protein may be tested for interaction with a test RNA or may be known to bind a specific RNA.

The DNA-binding domain of the first hybrid protein and the transcriptional activation domain of the second hybrid protein may be derived from transcriptional activators having separate DNA-binding and transcriptional activation domains. Separate DNA-binding and transcriptional activation domains are known to be found in the yeast GAL4 protein, and are also known in many transcription proteins. Many other proteins involved in transcription also have separable binding and transcriptional activation domains which make them useful for the present invention.

However, neither domain need come from a bona fide transcriptional activator. For example, LEX A, a DNA-binding protein without an activator activity, functions as the DNA binding domain in the first hybrid protein described below in the Examples. Therefore, in another embodiment, the DNA-binding domain and the transcriptional activation domain may be from different proteins.

The first or second hybrid protein may be encoded on a library of plasmids that contain genomic, cDNA or synthetically generated DNA sequences fused to the DNA sequence encoding the transcriptional activation domain.

A third chimeric gene is provided which is capable of being expressed as RNA in the host cell. The third chimeric gene contains a DNA sequence that encodes a hybrid RNA. The hybrid RNA contains a first RNA sequence that is capable of binding to either the first or second RNA-binding protein and a second test RNA sequence that is to be tested for interaction with the RNA-binding protein not bound to the first sequence. FIG. 2 and SEQ ID NO:7 are examples of an exemplary hybrid RNA. The RNA depicted in FIG. 2 and SEQ ID NO:7 comprises both the TAR sequence (capable of binding the HIV TAT protein) and the MS2 coat protein-binding sites.

A preferred promoter for this construct is found in the vector pIIIEx423RPR (Good, et al., Gene 151:209–214, 1994).

In one embodiment, the first, second and third chimeric genes are introduced into the host cell in the form of plasmids. Preferably, however, two of the chimeric genes are present in a chromosome of the host cell and the third chimeric gene is introduced into the host cell as part of a plasmid. Alternatively, two of the chimeric genes could be present in the chromosome and a third on a plasmid.

The interaction between the two hybrid proteins and the hybrid RNA in the host cell, therefore, causes the transcriptional activation domain to activate transcription of the detectable gene. The host cell is subjected to conditions under which the first hybrid protein, the second hybrid protein and the hybrid RNA are expressed in sufficient quantity for the detectable gene to be activated. The cells are then tested for expression of the detectable gene to a greater degree than in the absence of an interaction between both the first test protein and the hybrid RNA and the second test protein and the hybrid RNA.

Thus, interactions between an RNA molecule and a RNA-binding protein can be tested.

4. Kits

The method of the present invention, as described above, may be practiced using a kit. We envision that the useful kit of the present invention would comprise at least one container, two vectors, and a host cell. The kit will allow one to insert test sequences in either the first, second or third chimeric gene. Typically, one would wish to have the ability to insert both a test RNA sequence and a test RNA-binding protein in vectors that would be provided by the kit. The DNA sequence encoding the DNA-binding domain and a first RNA-binding protein may comprise part of a vector or may be included on the host cell's chromosomal DNA. Two other vectors included with the kit must include one vector with an activation domain, and one vector encoding a first RNA sequence known to bind the first specific first RNA-binding protein. Each of these vectors will have a restriction enzyme site, preferably unique, so that a DNA encoding a test RNA-binding domain and test RNA sequence can be inserted.

For example, the first chimeric gene contains a promoter and may include a transcription termination signal functionally associated with the first chimeric gene in order to direct the transcription of the first chimeric gene. The first chimeric gene includes a DNA sequence that encodes a DNA-binding domain and a first RNA-binding protein in such a manner that the first RNA-binding protein is expressed as part of a hybrid protein with the DNA-binding domain. The chimeric gene also includes a means for replicating itself in the host cell and in bacteria.

As described above, the first chimeric gene may be part of a vector or may be incorporated in the host chromosomal DNA. If the first chimeric gene is part of a vector, also included on the first vector is a first marker gene, the expression of which in the host cell permits selection of cells containing the first marker gene from cells that do not contain the first marker gene. Preferably, the first vector is a plasmid.

The kit also includes a vector which contains a second chimeric gene. The second chimeric gene also includes a promoter and a transcription termination signal to direct transcription. The second chimeric gene also includes a DNA sequence that encodes a transcriptional activation domain and a unique restriction site(s) to insert a DNA sequence encoding a second RNA-binding protein or protein fragment into the vector, in such a manner that the second RNA-binding protein is capable of being expressed as part of a hybrid protein with the transcriptional activation domain.

The kit also includes a vector which contains a third chimeric gene. The third chimeric gene includes a promoter and transcriptional termination signal to direct transcription. The third chimeric gene also includes a DNA sequence designed to encode an RNA known to bind to either the first or second RNA binding protein. The vector includes a convenient restriction enzyme site designed to allow incorporation of DNA sequences encoding test RNAs.

The DNA-binding domain of the first hybrid protein and the transcriptional activation domain of the second hybrid protein may be derived from transcriptional activators having separate DNA-binding and transcriptional activation domains.

These separate DNA-binding and transcriptional activation domains are also known to be found in the yeast GAL4 protein, and are known to be found in the yeast GCN4 and ADR1 proteins. Many other proteins involved in transcription also have separable binding and transcriptional activation domains which make them useful for the present invention.

In another embodiment, the DNA binding domain and the transcriptional activation domain may be from different transcriptional activators. Alternatively, the DNA-binding domain and transcriptional activation domain may be obtained from separate proteins with unrelated functions.

The second hybrid protein may be encoded on a library of plasmids that contain genomic, cDNA or synthetically generated DNA sequences fused to the DNA sequence encoding the transcriptional activation domain.

The second and third vectors further include a means for replicating in the host cell and in bacteria. The second and third vectors also include marker genes, the expression of which in the host cell permits selection of cells containing the marker genes from cells that do not contain the marker genes.

The kit includes a host cell, preferably a yeast strain of *Saccharomyces cerevisiae* or *Schizosaccharomyces pombe*. The host cell contains the detectable gene having a binding site for the DNA-binding domain of the first hybrid protein. The binding site is positioned so that the detectable gene expresses a detectable protein when the detectable gene is activated by the transcriptional activation domain encoded by the second vector. Activation of the detectable gene is possible when the transcriptional activation domain is in sufficient proximity to the detectable gene.

Accordingly in using the kit, the interaction of the first RNA-binding domain, the second RNA-binding domain and the hybrid RNA in the host cell causes a measurably greater expression of the detectable gene than when the DNA-binding domain and the transcriptional activation domain are present in the absence of an interaction between the RNA-binding domain and the hybrid RNA. The detectable gene may encode an enzyme or other product that can be readily measured. Such measurable activity may include the ability of the cell to grow only when the marker gene is transcribed or the presence of detectable enzyme activity only when the marker gene is transcribed. Various other markers are well known within the skill of workers in the art.

The cells containing the two hybrid proteins and the hybrid RNA are incubated in an appropriate medium and the culture is monitored for the measurable activity. A positive test for this activity is an indication that the first and second RNA-binding domains have interacted with the hybrid RNA. Such interaction brings their respective DNA-binding and transcriptional activation domains into sufficiently close proximity to cause transcription of the marker gene.

In one preferred embodiment, the two hybrid proteins contain domains of a yeast transcriptional activator, the GAL4 protein. A yeast strain is used that carries several genes under the regulation of UAS$_G$ and therefore able to bind the GAL4 DNA-binding domain. One of these genes is GAL1-lacZ, which contains the *E. coli* lacZ gene encoding β-galactosidase. Therefore, β-galactosidase activity, detected by liquid assay or by colony color on appropriate media, is a measure of GAL4 function. Growth of the yeast on galactose requires the transcription of genes regulated by GAL4 and is also a measure of GAL4 function. The host yeast strain carries a deletion of the chromosomal GAL4 gene, such that any GAL4 function must be due to that encoded by the introduced plasmids.

5. Other Embodiments

The present invention has several other embodiments useful for testing and exploring RNA-protein and RNA—RNA interactions. In one embodiment, the present invention may be used to determine whether a specific substance is an inhibitor or modulator of RNA-protein interactions. One would perform the method of the present invention in both the presence and the absence of the test substance and determine the expression level of the detectable gene. If the detectable gene is not expressed in the presence of the substance and is expressed in the absence of the substance, then the substance may have inhibited either of the RNA-protein interactions. Subsequent screening will be needed to determine whether the substance interferes with binding of the first hybrid protein to DNA, the interaction between the first hybrid protein and the hybrid RNA, interaction between the second hybrid protein and the hybrid RNA, or with the activation. Controls using suitable combination of two-hybrid and three-hybrid plasmids will identify those compounds that affect the interaction of interest and merit further study.

In another embodiment, the present invention is a method of optimizing an RNA sequence for high affinity protein binding. One would compare various RNA sequences in the method of the present invention to determine which RNA sequence bound with highest affinity. This would be done by comparing the results of the method of the present invention performed with hybrid RNAs with substitute RNA sequences. Preferably, these sequences would be only slightly altered from each other, i.e., one or two nucleotides, to fine-tune the RNA sequence needed for highest affinity protein binding.

The present invention is also a method of assaying RNA—RNA interactions. One would create both a first and second hybrid RNA. The first hybrid RNA would comprise a first RNA sequence designed to bind the first hybrid protein and a second RNA sequence to be tested. The second hybrid RNA would comprise a third RNA sequence designed to bind the second hybrid protein and a fourth RNA sequence to be tested. The third and fourth RNA sequences would have to interact for transcriptional activation to take place. Thus, one could determine whether or not two RNA sequences are capable of interacting.

EXAMPLES

1. In General

In the yeast two-hybrid system, (Fields, et al., *Nature* 340:245–246, 1989; Chien, et al., *Proc. Nat'l. Acad. Sci. U.S.A.* 88:9578–9582, 1991) a protein—protein interaction brings together a DNA-binding domain and a transcriptional activation domain. In the three-hybrid approach of the present invention, the DNA-binding and activation domains are brought together by a bifunctional RNA (called here a "hybrid RNA") that binds to each of the two hybrid proteins.

FIGS. 1A–C is a schematic diagram of the strategy to detect RNA-protein interactions. In our Examples described below, we created a hybrid RNA with two known protein-binding sequences and hybrid proteins known to bind these RNA sequences. A hybrid protein containing a DNA-binding domain (e.g. LexA) with RNA-binding protein 1 (e.g. MS2 coat protein) localized to the promoter of an appropriate reporter gene. A second hybrid protein containing a transcriptional activation domain (e.g. from Gal4) with RNA-binding protein 2 (e.g. HIV TAT protein) activated transcription of the reporter gene when in close proximity to the gene's upstream regulatory sequences. A hybrid RNA containing sites recognized by the two RNA-binding proteins linked the two hybrid proteins to one another, and the tripartite complex resulted in detectable expression of the reporter gene.

2. Methods

The MS2 coat protein gene was amplified by PCR from the plasmid PKCO, an overexpression plasmid for coat protein similar to pTCT5 (Gott, et al., *Biochem.* 30:6290–6295, 1991) using the following primers:

5' CAGGTGGATCCATATGGCTTCTAACTTTACT 3' (SEQ ID NO:1) and

5' TGCTAGGATCCTTAGTAGATGCCGGAGTT 3' (SEQ ID NO:2).

The PCR product was digested with BamHI and ligated to the vector pBTM116 (Bartel, et al., *Cellular Interactions in Development*, ed. D. A. Hartley, pp. 153–179, Oxford University Press, Oxford, 1993) to generate the plasmid p62.

The HIV TAT protein gene was amplified by PCR from the plasmid pBC12/CMV/t2 (Cullen, *Cell* 46:973–982, 1986) using the primers below:

5' AGTCGGGATCCTAATGGAGCCAGTAGATCCT 3' (SEQ ID NO:3) and

5' GTGACGGATCCTTACTGCTTTGATAGAGAAAC 3' (SEQ ID NO:4).

The product was digested with BamHI and ligated to the vector pACT (Durfee, et al., *Genes Dev.* 7:555–569, 1993) to generate the plasmid p201.

The HIV TAR element was prepared by annealing the oligonucleotides below:

5' CCCGGGTCTCTCTGGTTAGACCAGATCT- GAGCCTGGGAGCTC 3' (SEQ ID NO:5) and

5' ATCGGGTTCCCTAGTTAGCCA- GAGAGCTCCCAGGCTCAGATCT 3' (SEQ ID NO:6). After annealing, the 3' ends were filled in with DNA polymerase I (Klenow fragment), and ligated into the EcoRV site of pBluescriptII KS(+) (Stratagene) to produce pBS-TAR(+). The orientation of the TAR element is the same as that of the lacZ gene.

To combine TAR with MS2 coat protein binding sites, a BamHI-HindIII fragment containing two tandem coat protein binding sites (Bardwell, et al., *Nucl. Acids Res.* 18:6587–6594, 1987) was cloned into the EcoRV site of pBS-TAR(+) to yield pTAR17-1. The SmaI fragment of pTAR17-1, containing the TAR sequence and coat protein binding sites, was cloned into the SmaI site of PTET, which is essentially pBluescriptII KS(+) with its Amp$^r$ gene inactivated and a Tet$^r$ gene inserted at the AflII site, to yield pTAR17-6. The orientation of the RNA sites is the same as that of the lacz gene.

Finally, the EcoRI fragment of pTAR17-6, containing the TAR sequence and coat protein binding sites, was cloned into the EcoRI site of pIIIEx423RPR (Good, et al., *Gene* 151:209–214, 1994), in both orientations, to generate pTAR17-11 and pTAR17-12. In pTAR17-11, the RNase P promoter drives synthesis of a predicted 316 nucleotide transcript containing, from 5' to 3', 84 nucleotides of the leader sequence, 14 nucleotides of linker sequence, 58 nucleotides of TAR, 32 nucleotides of linker region, 60 nucleotides of the MS2 recognition sequence, 27 nucleotides of linker region, and 41 nucleotides of terminator sequence of RNase P. The two coat protein binding sites have the U to C change that enhances binding to coat protein.

Three colonies from each transformation were plated on media lacking tryptophan, leucine, and histidine, and containing 25 mM 3-aminol,2,4-triazole and 300 µg/ml 5-bromo-4-chloro-3-indolyl-β-D-galactoside.

3. Analysis of the Interaction of TAT Protein with TAR RNA

In the method of the present invention, one hybrid protein consists of a known RNA-binding protein fused to a DNA-binding domain. For this purpose we chose to join the coat protein of bacteriophage MS2 to the DNA-binding protein, LexA. The MS2 coat protein, like the nearly identical protein from R17, recognizes a 21 nucleotide RNA stem-loop in its genome with high affinity (1–10 nM) (Uhlenbeck, et al., *J. Biomol. Struct. Dynamics* 1:539–552, 1983). The LexA protein binds tightly to a 17 base pair DNA sequence, and is commonly used to tether proteins to DNA. The LexA-coat protein hybrid anchors the two hybrid proteins and the hybrid RNA to a reporter gene regulated by LexA binding sites. The vector carrying this LexA-coat protein hybrid, pBTM116 (Bartel, et al., *Cellular Interactions in Development* (ed. D. A. Hartley) p. 153–179, Oxford Univ. Press, Oxford, 1993) also carries the yeast selectable gene TRP1.

The second hybrid protein consists of a second RNA binding domain fused to a transcriptional activation domain. In this particular case, we sought to analyze the interaction of the HIV TAT protein with its RNA target, TAR, which comprises the first 59 nucleotides of all HIV-1 transcripts. (Cullen, *Micro. Rev.* 56:375–394, 1992.) We thus generated a fusion of the TAT protein to the Gal4 activation domain, using the vector pACT (Durfee, et al., 1993, supra), which carries the LEU2 gene.

A third plasmid encodes a hybrid RNA, containing two copies of the MS2 coat protein binding site and a single TAR element. Two coat protein binding sites were used because binding to adjacent sites is cooperative. (Witherell, et al., *Biochem.* 29:11051–11057, 1990; Bardwell, et al., *Nucl. Acids Res.* 18:6587–6594, 1987.) Similarly, a variant site, containing a single base change, was used because it enhances binding of coat protein 5- to 10-fold. (Lowary, et al., *Nucl. Acids Res.* 15:10483–10493, 1987.)

The hybrid RNA was expressed from the vector pIIIEx423RPR (Good, et al., 1994, supra), which uses the RNA polymerase III promoter and terminator from the *S. cerevisiae* RNase P RNA gene (RPR1) to generate high levels of small RNAs in yeast that do not enter pre-mRNA processing pathways. This is a high copy vector containing the selectable gene HIS3. Many other RNA-binding proteins and RNA sequences could be used in this method in place of TAT and TAR.

We introduced combinations of the three plasmids described above, as well as appropriate control plasmids, into the yeast reporter strain L40 (Vojtek, et al., *Cell* 74:205–214, 1993), which contains a lacZ gene whose expression is regulated by LexA binding sites in the 5' flanking sequence. The strain was transformed by selection for tryptophan, leucine and histidine prototrophy, and transformants were assayed for lacZ expression by a plate assay and by liquid assay.

Table 1, below, tabulates β-galactosidase enzyme units for some of the transformed yeasts. By liquid assays with chlorophenol red-β-D-galactopyranoside as substrate, (Iwabuchi, et al., *Oncogene* 8:1693–1696, 1993) the transformants containing the coat, TAT and RNA hybrids produced approximately 500 units of β-galactosidase activity, which was more than 20-fold greater than any of the control transformants.

As shown in Table 1, transformants carrying the LexA-coat protein and activation domain-TAT protein hybrids along with the hybrid RNA showed readily detectable β-galactosidase activity. In the absence of any one of these three hybrid components, transformants displayed little activity, indicating that the hybrid RNA must be capable of binding simultaneously to both hybrid proteins, and that the resultant RNA-protein complex can trigger transcription.

TABLE 1

| β-galactosidase enzyme units | Plasmids Transformed into Yeast |
|---|---|
| 500 Units | All three plasmids |
| 7 Units | LEXA vector + TAT/ad + MS$_2$/TAR RNA |
| 9 Units | LEXA vector + TAT/ad + antisense MS$_2$/TAR RNA |
| 23 Units | LEXA/MS$_2$ + ad + MS$_2$/TAR RNA |

Referring to Table 1, the controls also show the following: First, introduction of the LexA-coat protein hybrid, in the absence of either one of the other two required components, did not lead to significant β-galactosidase activity. Thus, the coat protein does not itself possess a transcriptional activation domain. Second, introduction of the coat protein hybrid with only the hybrid RNA resulted in little transcriptional activity. It follows that if the RNA bound to the coat protein, as dramatically appears likely, then it did not activate transcription; it should, however, provide a highly negatively charged surface as appears to be important for transcriptional stimulation by several activator proteins. Third, the coat protein and TAT hybrids, along with the RNase P promoter vector expressing the hybrid RNA in the antisense orientation, did not lead to transcription. Thus coat protein and TAT, as expected, do not bind to each other to result in transcription by virtue of protein—protein interaction. Additionally, this control indicates that the 125 bases of RNA from the RPR1 promoter and terminator that will also be present in the hybrid RNA do not mediate interactions with the hybrid proteins. Finally, the hybrid RNA and activation domain-TAT hybrid did not result in transcription in the absence of the LexA-coat protein hybrid.

We claim:

1. A hybrid RNA molecule selected by detecting an interaction between an RNA-binding domain and a test RNA molecule, the method comprising:
    (1) introducing into a host cell:
        (a) a detectable gene wherein the detectable gene expresses a detectable protein when the detectable gene is activated by an amino acid sequence including a transcriptional activation domain when the transcriptional activation domain is in sufficient proximity to the detectable gene;
    (b) a first chimeric gene that encodes a first hybrid protein comprising:
        (i) a DNA-binding domain that recognizes a binding site on the detectable gene in the host cell; and
        (ii) a first RNA binding domain;
    (c) a second chimeric gene that encodes a second hybrid protein comprising:
        (i) a transcriptional activation domain; and
        (ii) a second RNA-binding domain;
    (d) a third chimeric gene that encodes said hybrid RNA comprising:

(i) a first RNA sequence that binds one of the first or second RNA-binding domains; and (ii) a second RNA sequence to be tested for interaction with the RNA-binding domain not bound to the first RNA sequence;

wherein interaction between both the first RNA-binding domain and the hybrid RNA and the second RNA-binding domain and the hybrid RNA in the host cell causes the transcriptional activation domain to activate transcription of the detectable gene;

(2) subjecting the host cell to conditions under which the first hybrid protein, the second hybrid protein, and said hybrid RNA are expressed in sufficient quantity for the detectable gene to be activated;

(3) determining whether the detectable gene has been expressed to a degree greater than expression of the detectable gene in the absence of interactions between both the first RNA-binding domain and said hybrid RNA and the second RNA-binding domain and said hybrid RNA; and (4) selecting said hybrid RNA.

* * * * *

UNITED STATES PATENT AND TRADEMARK OFFICE
CERTIFICATE OF CORRECTION

PATENT NO. : 5,750,667
DATED : May 12, 1998
INVENTOR(S) : Marvin P. Wickens, et al.

It is certified that error appears in the above-indentified patent and that said Letters Patent is hereby corrected as shown below:

At column 1, line 5, please insert the following:

This invention was made with United States Government support awarded by the National Institutes of Health (NIH), Grant Nos. GM31892 and GM50942. The United States Government has certain rights in this invention.

Signed and Sealed this

Eighteenth Day of August, 1998

Attest:

BRUCE LEHMAN

Attesting Officer

Commissioner of Patents and Trademarks